(12) United States Patent
Hoppmann et al.

(10) Patent No.: US 9,675,322 B2
(45) Date of Patent: Jun. 13, 2017

(54) ENHANCED ULTRASOUND DEVICE AND METHODS OF USING SAME

(71) Applicants: Richard A. Hoppmann, Columbia, SC (US); Shaun Riffle, Lexington, SC (US); Victor Rao, Columbia, SC (US); Stephen Harris, Columbia, SC (US); Duncan Howe, Hopkins, SC (US); Mary Beth Poston, Columbia, SC (US)

(72) Inventors: Richard A. Hoppmann, Columbia, SC (US); Shaun Riffle, Lexington, SC (US); Victor Rao, Columbia, SC (US); Stephen Harris, Columbia, SC (US); Duncan Howe, Hopkins, SC (US); Mary Beth Poston, Columbia, SC (US)

(73) Assignee: University of South Carolina, Columbia, SC (US)

( * ) Notice: Subject to any disclaimer, the term of this patent is extended or adjusted under 35 U.S.C. 154(b) by 159 days.

(21) Appl. No.: 14/261,773

(22) Filed: Apr. 25, 2014

(65) Prior Publication Data

US 2014/0323865 A1    Oct. 30, 2014

Related U.S. Application Data

(60) Provisional application No. 61/816,447, filed on Apr. 26, 2013.

(51) Int. Cl.
*A61B 8/00* (2006.01)
*A61B 8/14* (2006.01)
*A61B 8/08* (2006.01)

(52) U.S. Cl.
CPC .............. *A61B 8/14* (2013.01); *A61B 8/4416* (2013.01); *A61B 8/5261* (2013.01)

(58) Field of Classification Search
None
See application file for complete search history.

(56) References Cited

U.S. PATENT DOCUMENTS

| 5,501,222 | A | * | 3/1996 | Briggs | G01S 15/8993 |
| | | | | | 600/453 |
| 5,868,579 | A | | 2/1999 | Lampotang et al. | |
| 6,213,944 | B1 | * | 4/2001 | Miller | G01S 7/52087 |
| | | | | | 386/E9.013 |

(Continued)

FOREIGN PATENT DOCUMENTS

| EP | 2408176 A1 | 1/2012 |
| WO | WO 02/07586 | 1/2002 |

(Continued)

*Primary Examiner* — Tse Chen
*Assistant Examiner* — Joanne Hoffman
(74) *Attorney, Agent, or Firm* — Dority & Manning, P.A.

(57) ABSTRACT

In one aspect, an enhanced ultrasound device may generally comprise an ultrasound probe including a housing and at least one transducer element disposed within the housing. The ultrasound probe may be configured to generate ultrasound image signals associated with an object being imaged. In addition, the device may include an acoustic receiver associated with the ultrasound probe. The acoustic receiver may be configured to generate auscultation signals associated with sounds generated by the object as the object is being imaged using the ultrasound probe.

14 Claims, 6 Drawing Sheets

(56) References Cited

U.S. PATENT DOCUMENTS

| | | | |
|---|---|---|---|
| 6,454,716 B1 * | 9/2002 | Zumeris | A61B 8/02 600/453 |
| 6,781,522 B2 | 8/2004 | Sleva et al. | |
| 7,146,184 B1 | 12/2006 | Tsitsiashvili | |
| 7,750,537 B2 * | 7/2010 | Hossack | B06B 1/0629 310/334 |
| 7,792,314 B2 * | 9/2010 | Ramakrishnan | H04B 17/391 367/93 |
| D631,246 S | 1/2011 | Boettner | |
| 8,418,852 B2 | 4/2013 | Ziemba | |
| D688,655 S | 8/2013 | Rey-Hipolito et al. | |
| 8,499,933 B2 | 8/2013 | Ziemba | |
| 2008/0281206 A1 | 11/2008 | Bartlett et al. | |
| 2009/0099446 A1 * | 4/2009 | Frigstad | A61B 8/14 600/437 |
| 2009/0171212 A1 | 7/2009 | Garon | |
| 2009/0279708 A1 | 11/2009 | Habboushe | |
| 2010/0055657 A1 | 3/2010 | Goble et al. | |
| 2010/0179428 A1 | 7/2010 | Pedersen et al. | |
| 2010/0203487 A1 | 8/2010 | Cyr et al. | |
| 2010/0279262 A1 | 11/2010 | Lecat | |
| 2011/0089077 A1 | 4/2011 | Ziemba | |
| 2011/0284407 A1 | 11/2011 | Connolly | |
| 2011/0303560 A1 | 12/2011 | Friedman et al. | |
| 2011/0306025 A1 | 12/2011 | Sheehan et al. | |
| 2012/0058457 A1 | 3/2012 | Savitsky | |
| 2012/0244918 A1 | 9/2012 | Hall | |
| 2012/0264491 A1 | 10/2012 | Singhal | |
| 2014/0066142 A1 | 3/2014 | Gipson | |

FOREIGN PATENT DOCUMENTS

| WO | WO 2010/093887 | 8/2010 |
|---|---|---|
| WO | WO 2010/126396 | 11/2010 |
| WO | WO 2011/124922 | 10/2011 |

* cited by examiner

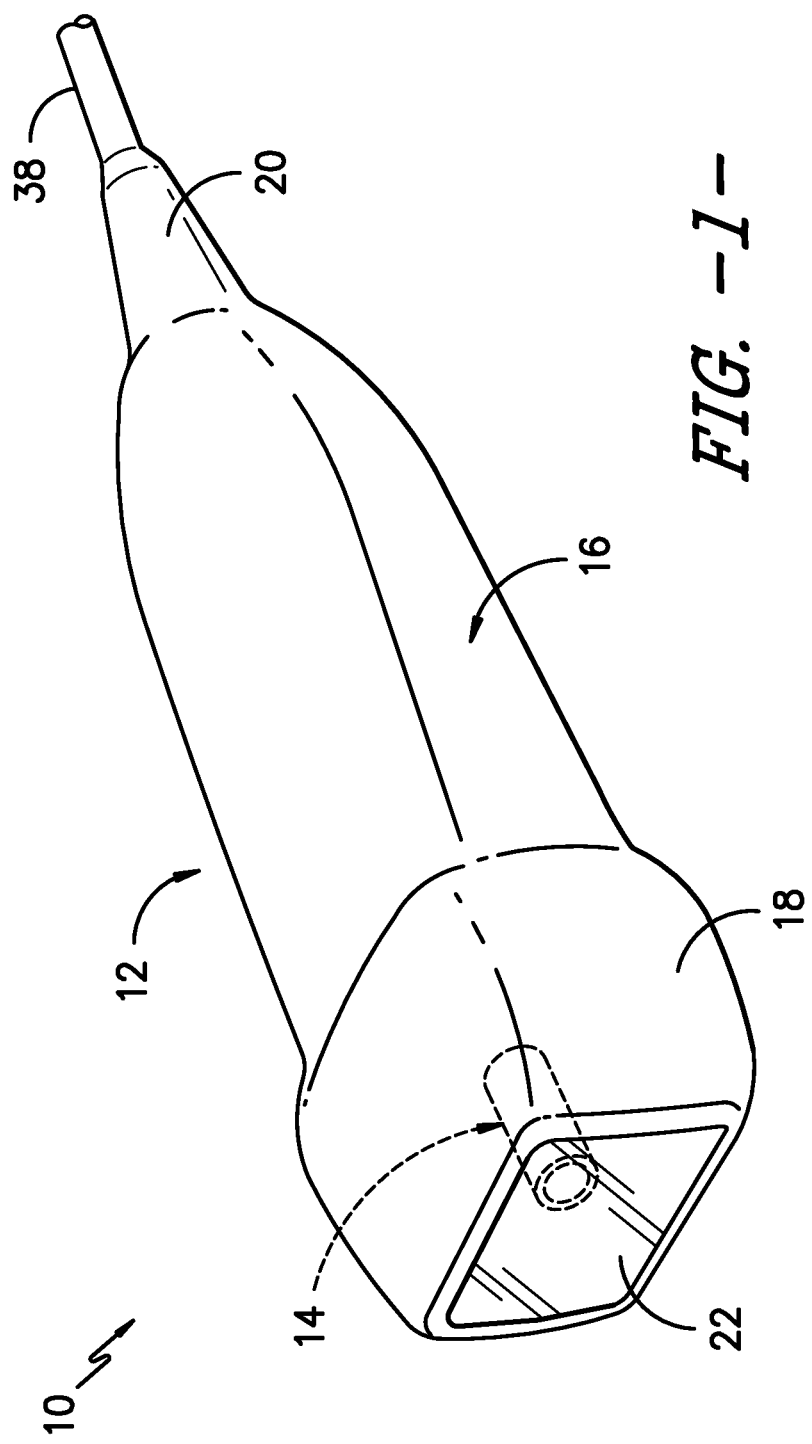

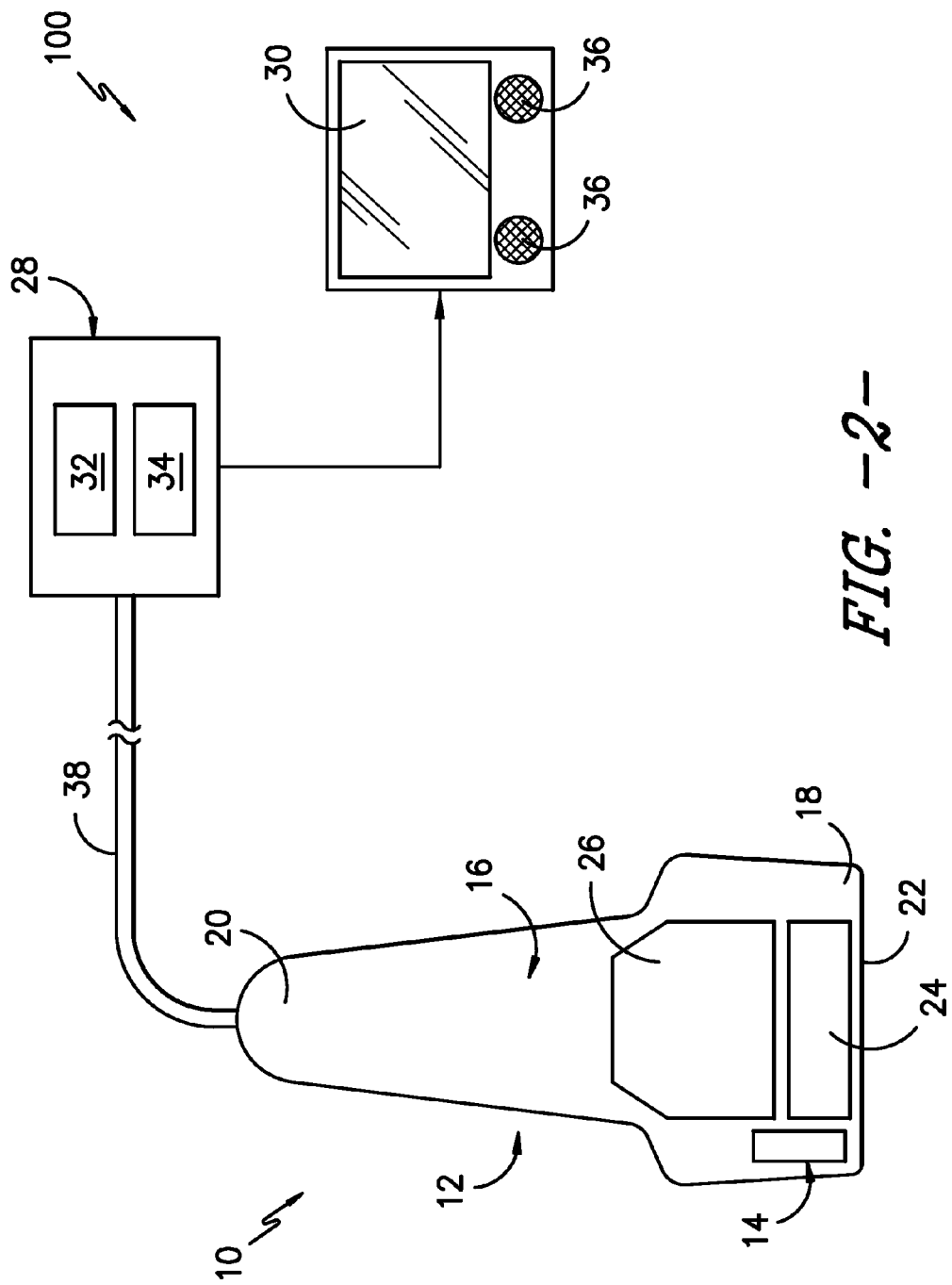
FIG. -2-

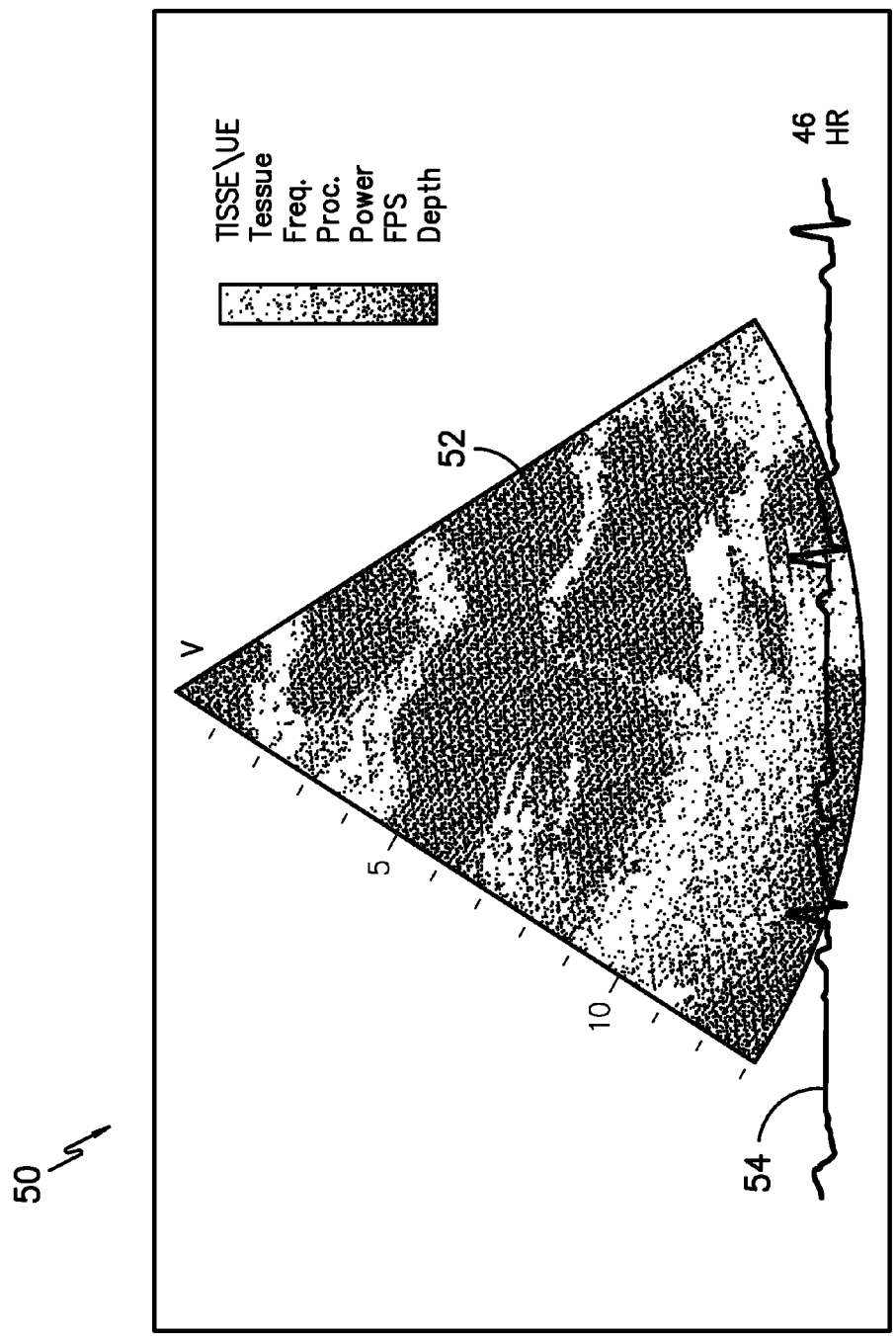
FIG. -3-

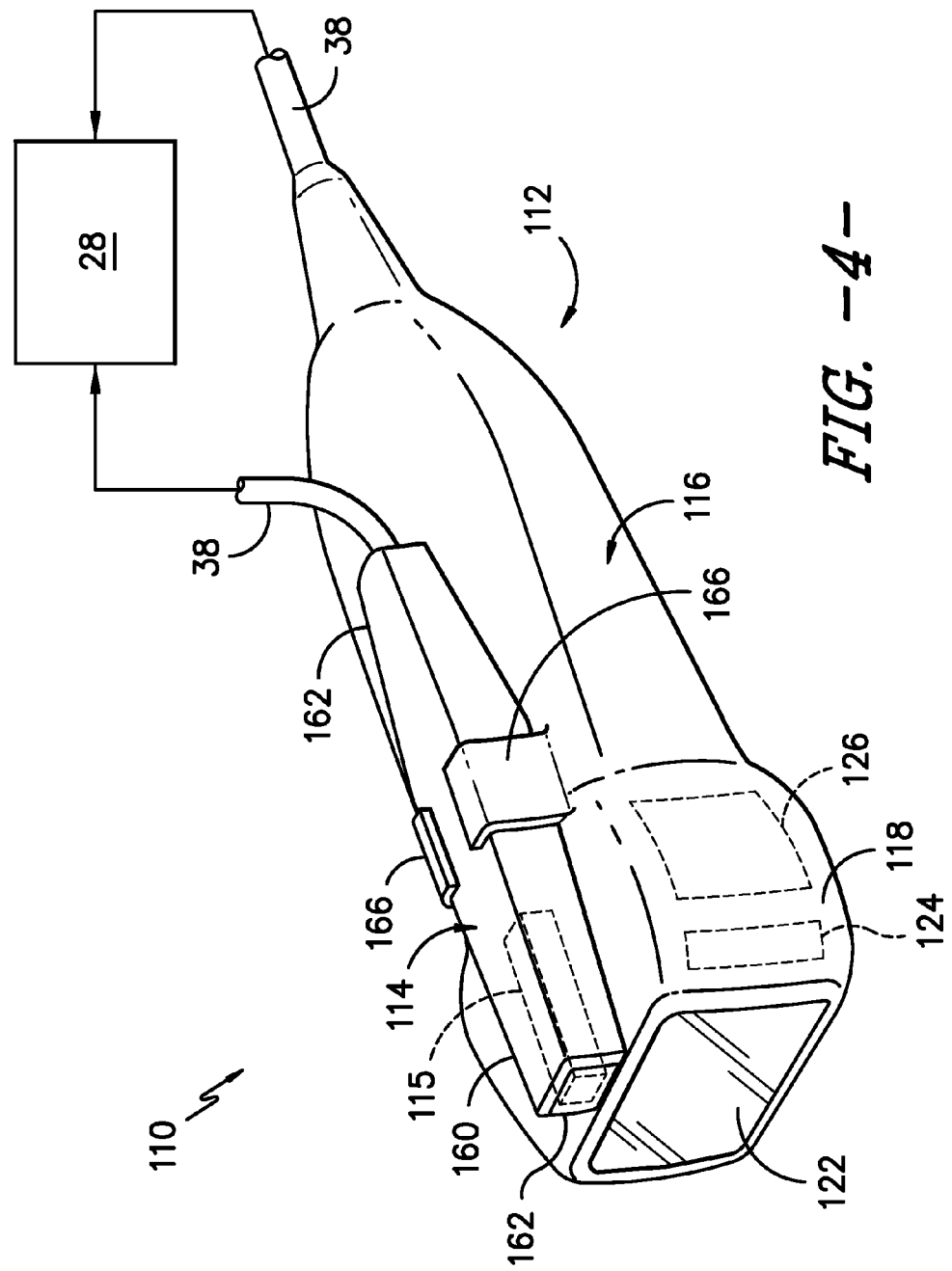
FIG. -4-

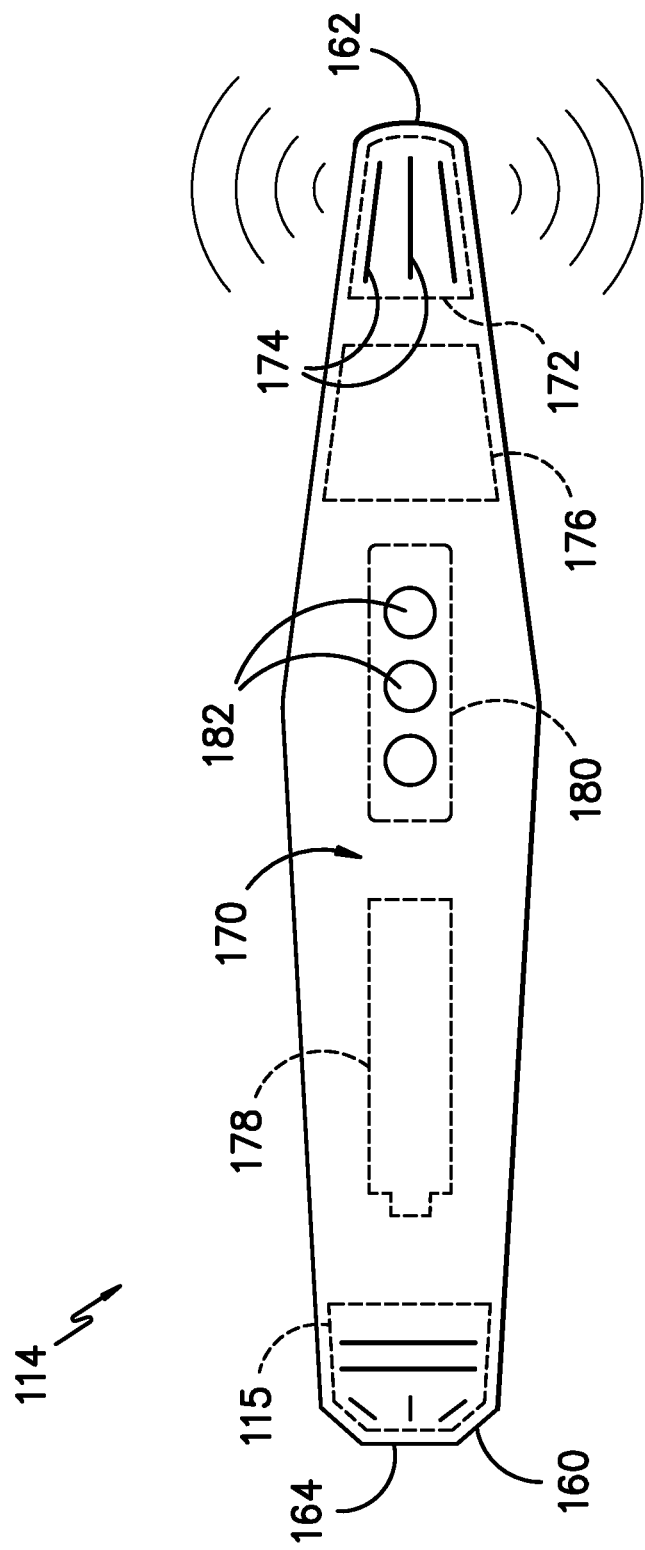
FIG. -5-

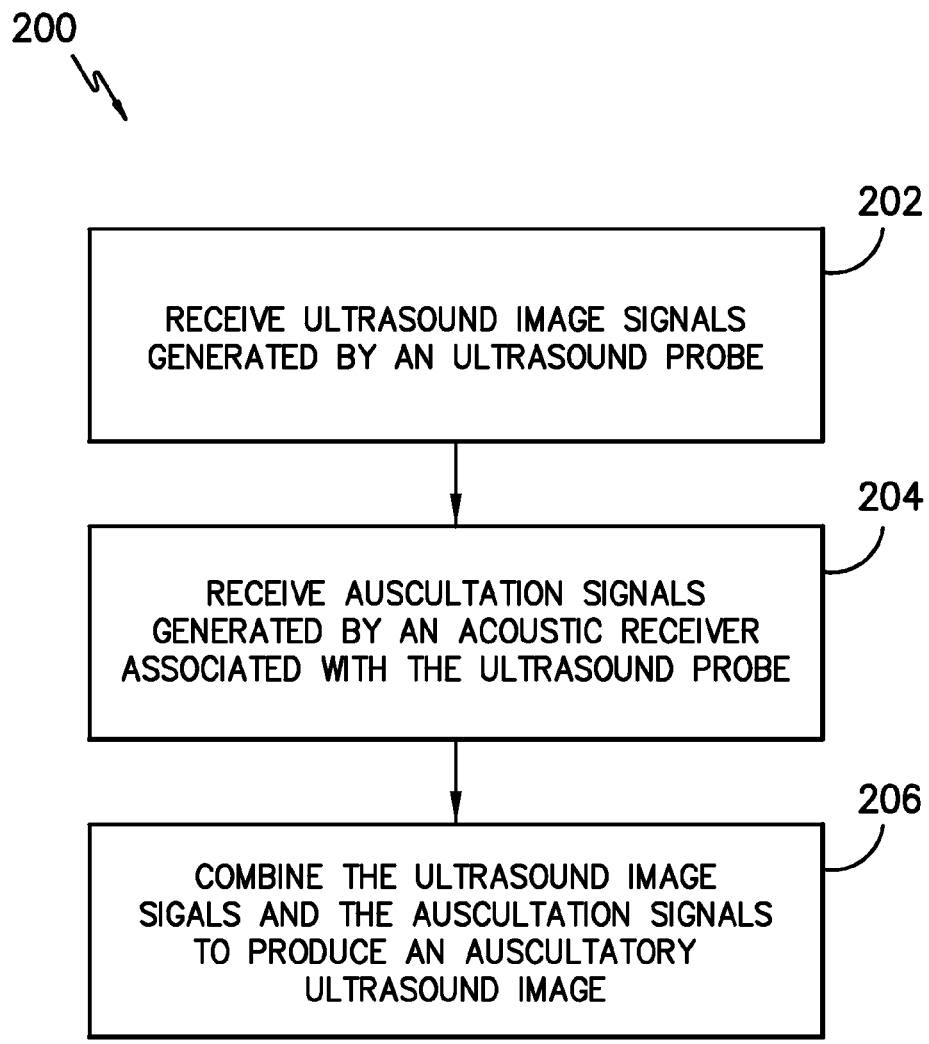
FIG. -6-

ENHANCED ULTRASOUND DEVICE AND METHODS OF USING SAME

CROSS-REFERENCE TO RELATED APPLICATIONS

This application is based upon and claims priority to U.S. Provisional Patent Application No. 61/816,447, filed on Apr. 26, 2013 and entitled "Enhanced Ultrasound Probe and Methods of Using Same," the disclosure of which is hereby incorporated by reference herein in its entirety for all purposes.

FIELD

The present disclosure relates generally to devices, systems and methods for ultrasound and, more particularly, to an enhanced ultrasound device for conducting auscultatory ultrasounds.

BACKGROUND OF THE INVENTION

Traditionally, ultrasound examinations are conducted separate and apart from auscultatory examinations. In particular, physicians typically use a conventional ultrasound machine to generate and display ultrasound images of internal organs and/or other body parts desired to be imaged. However, conventional ultrasound machines do not allow for auscultatory sounds to be incorporated into the moving ultrasound image of the organ being viewed. Rather, to listen to the sounds generated by the heart, lung, and/or other internal organs, physicians typically must rely on the use a stethoscope. As a result, it is often difficult to accurately identify a given pathology, particularly a heart pathology.

Accordingly, an enhanced ultrasound device that allows for ultrasound and auscultatory examinations to be conducted simultaneously would be welcomed in the technology.

BRIEF DESCRIPTION OF THE INVENTION

Aspects and advantages of the invention will be set forth in part in the following description, or may be obvious from the description, or may be learned through practice of the invention.

In one aspect, the present subject matter is directed to an enhanced ultrasound device. The device may generally comprise an ultrasound probe including a housing and at least one transducer element disposed within the housing. The ultrasound probe may be configured to generate ultrasound image signals associated with an object being imaged. In addition, the device may include an acoustic receiver associated with the ultrasound probe. The acoustic receiver may be configured to generate auscultation signals associated with sounds generated by the object as the object is being imaged using the ultrasound probe.

In another aspect, the present subject matter is directed to a system for conducting auscultatory ultrasounds. The system may generally comprise an ultrasound probe including a housing and at least one transducer element disposed within the housing. The ultrasound probe may be configured to generate ultrasound image signals associated with an object being imaged. The system may also include an acoustic receiver associated with the ultrasound probe. The acoustic receiver may be configured to generate auscultation signals associated with sounds generated by the object as the object is being imaged using the ultrasound probe. In addition, the system may include a computing device communicatively coupled to the ultrasound probe and the acoustic receiver. The computing device may be configured to combine the ultrasound image signals and the auscultation signals to produce an auscultatory ultrasound image. The auscultatory ultrasound image may correspond to a synchronization of the sounds generated by the object with a moving ultrasound image produced based on the ultrasound image signals.

In a further aspect, the present subject matter is directed to a method for conducting auscultatory ultrasounds. The method may generally include receiving, with a computing device, ultrasound image signals generated by an ultrasound probe that are associated with an object to be imaged and receiving auscultation signals generated by an acoustic receiver associated with the ultrasound probe. The auscultation signals may be associated with sounds generated by the object as the object is being imaged using the ultrasound probe. In addition, the method may include combining the ultrasound image signals and the auscultation signals to produce an auscultatory ultrasound image. The auscultatory ultrasound image may correspond to a synchronization of the sounds generated by the object with a moving ultrasound image produced based on the ultrasound image signals.

Other exemplary aspects of the present subject matter are directed to other devices, systems, and methods for conducting auscultatory ultrasounds.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of an enhanced ultrasound device in accordance with aspects of the present subject matter;

FIG. 2 illustrates a schematic view of one embodiment of a system for conducting auscultatory ultrasounds, particularly illustrating a schematic view of the various components that may be included within and/or coupled to the enhanced ultrasound device shown in FIG. 1;

FIG. 3 illustrates a snapshot view of one example of an auscultatory ultrasound image in accordance with aspects of the present subject matter;

FIG. 4 illustrates a perspective view of another embodiment of an enhanced ultrasound device in accordance with aspects of the present subject matter;

FIG. 5 illustrates a top view of one embodiment of a suitable auscultation device that may form part of the enhanced ultrasound device shown in FIG. 4;

FIG. 6 illustrates a flow diagram of one embodiment of a method for conducting auscultatory examinations.

DETAILED DESCRIPTION OF THE INVENTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to devices, systems and methods for ultrasound. Specifically, in several embodiments, the present subject matter is directed to an enhanced ultrasound device for conducting auscultatory ultrasounds. For example, as will be described below, the disclosed device may include an ultrasound probe having an auscultation-related component(s) and/or a separate auscultation device associated therewith. In particular, in one embodiment, an acoustic receiver may be integrated into or otherwise incorporated within a given ultrasound probe to allow for auscultatory sounds to be captured and recording simultaneously with the capturing of ultrasound images. Alternatively, a separate auscultation device may be secured to a given ultrasound probe to allow for the performance of a simultaneous ultrasound and auscultatory examination.

Regardless, the sounds captured by the auscultation component/device may be combined with the ultrasound image(s) provided by the ultrasound probe using a suitable computing device to produce an auscultatory ultrasound image(s) that links the ultrasound image(s) with the corresponding auscultatory sounds. For example, the disclosed system may allow for auscultatory sounds to be mapped onto a moving ultrasound image, such as by syncing the sounds produced by an internal organ being imaged (e.g., a heart) to the movement of such organ within the ultrasound image(s). Such mapping of auscultatory sound onto a moving ultrasound image may, in turn, enable physicians to precisely link physiologic and pathologic sounds to specific items in the ultrasound image, thereby allowing for a more accurate diagnosis and identification of pathology than can be provided by either ultrasound or auscultation alone. Moreover, the auscultatory ultrasound image(s) produced using the disclosed system may also be used as a teaching tool for medical students, physicians-in-training and/or other healthcare workers receiving instruction in ultrasonography.

Referring now to the drawings, FIGS. 1 and 2 illustrate one embodiment of an enhanced ultrasound device 10 in accordance with aspects of the present subject matter. Specifically, FIG. 1 illustrates a perspective view of the device 10 and FIG. 2 illustrates a schematic view of the device 10 shown in FIG. 1, particularly illustrating various components that may be included within the device 10. In addition, FIG. 2 illustrates one embodiment of a system 100 within which the disclosed device 10 may be utilized to allow auscultatory ultrasound examinations to be performed.

As shown, the enhanced ultrasound device 10 may generally include an ultrasound probe 12 for providing suitable electrical signals associated with ultrasound images of a specific body part(s) to be imaged, such as an internal organ or any other suitable internal body part(s). In addition, the device 10 may include one or more auscultation components 14 integrated into or otherwise incorporated within the ultrasound probe 12 for capturing auscultatory sounds generated by the body part(s) being imaged. Accordingly, the disclosed device 10 may allow for a simultaneous ultrasound and auscultatory examination to be performed on a patient. As will be described in greater detail below, the moving ultrasound images and sounds captured using the device 10 may be combined to produce an auscultatory ultrasound image(s), which may then be broadcast/displayed to a physician (and/or patient) for immediate analysis and/or stored for subsequent analysis.

It should be appreciated that the ultrasound probe 12 within which the auscultation component(s) 14 is integrated may generally correspond to any suitable probe or device known in the art for capturing ultrasound images. As such, the ultrasound probe 12 may generally include any or all of the components typically contained within such probes/devices. For instance, as shown in the illustrated embodiment, the ultrasound probe may include a housing 16 configured to serve as an outer casing for the various internal components of the probe 12. As is generally understood, the housing 16 may be configured to define any suitable size and/or shape depending on, for example, the size and/or shape of the internal components configured to be encased within the housing 16 and/or the intended use of the probe 12 (e.g., an internal probe or an external probe). However, in general, the housing may be configured to extend lengthwise between a detection end 18 and an opposite, non-detection end 20, with the detection end 20 generally being configured to be placed adjacent to and/or within the body of a patient to allow for an ultrasound examination to be conducted. For instance, as shown in the illustrated embodiment, the detection end 18 of the probe housing 16 may define a contact surface 22 configured to be positioned directly adjacent to a patient's skin when capturing ultrasound images from a location external to the patient's body.

Additionally, as particularly shown in FIG. 2, the ultrasound probe 12 may include one or more transducer elements 24 (e.g., an array of piezoelectric elements) disposed within the housing 16 at or adjacent to the detection end 18, such as at or adjacent to the contact surface 22. As is generally understood, the transducer element(s) 24 may be configured to both transmit and receive high frequency ultrasound waves. For example, in several embodiments, the transducer element(s) 24 may be configured to oscillate at a high frequency in response to an alternating current in order to produce high frequency sound waves that may be emitted in the direction of the particular body part(s) being imaged. In addition to emitting sound waves, the transducer element(s) 24 may also be configured to produce an electrical current when impinged by high frequency sound waves. Thus, as the high frequency sound waves emitted from the transducer element(s) 24 echo or reflect off of the body part(s) being imaged, the reflected sound waves impinging on the transducer element(s) 24 may be converted to electrical signals (hereinafter referred to as "ultrasound image signals") that can be used to produce a corresponding ultrasound image of the specific body part(s).

One of ordinary skill in the art should readily appreciate that the ultrasound probe 12 may also include any other suitable components that are typically contained within a standard ultrasound probe. For instance, as shown in FIG. 2, the ultrasound probe 12 may include a sound absorbing backing 26 to eliminate back reflections from the probe itself. Additionally, in some instances, the ultrasound probe 12 may include an acoustic lens (not shown) to assist in focusing the sounds waves emitted from the transducer element(s) 24 and/or an acoustic matching layer (not shown) to reduce the amount of external reflection and to increase the sensitivity of the probe 12.

Additionally, as shown in FIG. 2, the ultrasound probe 12 may be configured to be communicatively coupled to a suitable computing device 28. In general, the computing device 28 may be configured to transmit suitable control signals (e.g., in the form of electrical current signals) to the transducer element(s) 24 in order to cause such element(s) to produce the high frequency ultrasound waves. For example, the control signals generated by the computing device 28 may be specifically tailored such that the transducer element(s) 24 produce ultrasound waves at the desired amplitude, frequency and/or duration. In addition, the computing device 28 may also be configured to receive and process the ultrasound image signals emitted by the transducer element(s) 24 in response to the reflected sound waves. As is generally understood, the computing device 28 may be configured to process the ultrasound image signals received from the transducer element(s) 24 using known algorithms and techniques to produce a moving ultrasound image of the body part(s) being imaged. The ultrasound image may then be stored within the device's memory and/or transmitted to a suitable display device 30 (e.g., any suitable monitor, display screen or other output device for presenting visual information) for display to the physician and/or patient.

It should be appreciated that the computing device 28 may generally correspond to any suitable processor-based device. Thus, the computing device 28 may include, for example, one or more processor(s) 32 and associated memory device(s) 34 configured to perform a variety of computer-implemented functions (e.g., performing the methods, steps, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 34 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 34 may generally be configured to store suitable computer-readable instructions that, when implemented by the processor(s) 32, configure the computing device 28 to perform various functions including, but not limited to, converting the ultrasound image signals transmitted by the transducer element(s) 24 into a moving ultrasound image, combining the moving ultrasound image with auscultatory sounds to produce an auscultatory ultrasound image, recording the auscultatory ultrasound image within the memory device(s) 34 and/or transmitting the auscultatory ultrasound image to a suitable output device(s) (e.g., display/speaker) for broadcasting such image to a physician and/or patient.

It should also be appreciated that, in several embodiments, the computing device 28 may be incorporated into or otherwise form part of an ultrasound machine or console. In such embodiments, the console may also include various other components to assist in conducting an ultrasound examination, such as a keyboard, mouse and/or any other suitable input device, and a display (e.g., display device 30 shown in FIG. 2).

Additionally, as indicated above, the disclosed device 10 may also include an auscultatory component(s) 14 integrated into or otherwise incorporated within the ultrasound probe 12. Specifically, in several embodiments, the auscultatory component(s) may correspond to one or more acoustic receivers 14 disposed within the housing 16. In general, the acoustic receiver(s) 14 may correspond to any suitable receiver(s) capable of capturing auscultation sounds (i.e., the internal sounds of the body), such as any suitable unidirectional acoustic receiver(s) (e.g., a microphone). By unidirectional, it is meant that the acoustic receiver(s) 14 corresponds to an acoustic-to-electric transducer or sensor that is only configured to detect and convert sound waves into electrical signals as opposed to a bi-directional device (e.g., the transducer element(s) 24) that is able to both generate and detect sound waves. Thus, any sounds generated by the body part(s) being imaged using the ultrasound probe 16 may be detected by the acoustic receiver(s) 14 and converted into suitable electrical signals (hereinafter referred to as "auscultation signals") that can be subsequently recorded and/or broadcast (e.g., via speaker(s) 36 shown in FIG. 2).

It should be appreciated that the specific size and shape of the acoustic receiver(s) 14 may generally vary depending on, for example, any dimensional limitations or requirements associated with incorporating the receiver(s) 14 within the housing 16 and/or the desired performance of the receiver(s) 16. Those of ordinary skill in the art should readily appreciate that a significant number of acoustic receivers are commercially available that provide various options for receiver sizes and/or shapes, including relatively small acoustic receivers that provide for high quality sound capture.

In addition, it should be appreciated that, in general, the acoustic receiver(s) 14 may be configured to be positioned at any suitable location within the housing 16. However, in several embodiments, the placement of the acoustic receiver(s) 14 within the housing 16 may be carefully selected so as to provide for optimal performance of the receiver(s) 14. For instance, in a particular embodiment, it may be desirable to position the acoustic receiver(s) 14 at or adjacent to the detection end 18 of the housing 16, such as at or adjacent to the contact surface 22, in order to minimize the distance and/or potential for sound interference between the receiver(s) 14 and the body part(s) being imaged.

Similar to the transducer element(s) 24, the acoustic receiver(s) 14 may also be configured to be communicatively coupled to the computing device 28. Thus, the auscultation signals generated by the receiver(s) 14 may be transmitted to the computing device 28 for subsequent processing. For instance, the signals received from the acoustic receiver(s) 14 may be stored within the memory 34 of the computing device 28 and/or transmitted to a suitable speaker(s) 36 in order to reproduce the sounds captured by the receiver(s) 14. As shown in FIG. 2, in one embodiment, the speaker(s) 36 used to reproduce the auscultatory sounds may be incorporated within or may otherwise be associated with the display device 30 being used to display the moving ultrasound image. Alternatively, the speaker(s) 36 may correspond to a standalone speaker(s). Regardless, the sounds captured by the receiver(s) 14 may be synced with the moving ultrasound image and transmitted from the computing device 28 to the display device/speaker(s) 30, 36 to allow for the captured sounds to be broadcast simultaneously with the moving ultrasound image.

It should be appreciated that, in several embodiments, the enhanced ultrasound device 10 disclosed herein may be configured to be communicatively coupled to the computing device 28 via a wired connection. For instance, as shown in FIG. 2, a suitable communicative cable 38 may be coupled between the device 10 and the computing device 28 to allow the signals generated by the transducer element(s) 24 and the receiver(s) 14 to be transmitted to and received by the computing device 28. Alternatively, the enhanced ultrasound device 10 may be communicatively coupled to the computing device 28 via a wireless connection. In such an embodiment, the device 10 may, for example, include a wireless transmitter (not shown) disposed within the probe housing 16 that is configured to wirelessly transmit data using any suitable wireless communication protocol known in the art, such as the BLUETOOTH, WI-FI (802.11 b/g) and/or ZIG-BEE wireless communication protocols.

Referring now to FIG. 3, a snapshot of one example of an auscultatory ultrasound image 50 that may be produced using the disclosed enhanced ultrasound device 10 is illustrated in accordance with aspects of the present subject matter. Specifically, as indicated above, the computing device 28 may be configured to receive both the ultrasound image signals generated by the transducer element(s) 24 of the ultrasound probe 12 and the auscultation signals generated by the acoustic receiver(s) 14 and combine such signals to produce an auscultatory ultrasound image. In doing so, the computing device 28 may be configured to synchronize the ultrasound image signals and the auscultation signals with respect to time using known synchronization techniques and/or algorithms. Thus, the resulting auscultatory ultrasound image may generally correspond to a synchronization of the sounds generated by the body part(s) being imaged with the moving ultrasound image of such body part(s). As indicated above, such mapping or syncing of the auscultatory sounds with the moving ultrasound image may enable physicians to precisely link physiologic and pathologic sounds to specific items in the ultrasound image, thereby allowing for a more accurate diagnosis and identification of pathology.

As shown in FIG. 3, the auscultatory ultrasound image 50 may generally include both a moving ultrasound image of the body part(s) being imaged (indicated by snapshot 52 shown in FIG. 3) as well as the time synchronized auscultatory sounds that were produced by such body part(s) during imaging. Additionally, in several embodiments, the auscultatory ultrasound image 50 may also incorporate a display feature for providing a visual indication of the sounds generated by the body part(s) over time. For instance, as shown in FIG. 3, a sound graph 54 may be displayed on and/or adjacent to the moving ultrasound image 52 that provides, for example, a visual indication of the variation in the magnitude of the sound intensity or decibel level of the auscultatory sounds recorded over time.

Referring now to FIG. 4, a perspective view of another embodiment of an enhanced ultrasound device 110 is illustrated in accordance with aspects of the present subject matter. As shown in FIG. 4, the device 110 may generally include an ultrasound probe 112 configured the same as or similar to the ultrasound probe 12 described above with reference to FIGS. 1 and 2. Specifically, the ultrasound probe 112 may generally correspond to any suitable probe or device known in the art for capturing ultrasound images and, thus, may include many or all of the components typically contained within such probes/devices. For instance, as shown in the illustrated embodiment, the ultrasound probe 112 may include a housing 116 configured to serve as an outer casing or shell for the various internal components of the probe 112. In addition, the ultrasound probe 112 may include one or more transducer elements 124 (e.g., an array of piezoelectric elements) for transmitting and receiving high frequency sound waves, a sound absorbing backing 126 to eliminate back reflections from the probe 112 and/or any other suitable components (e.g., an acoustic lens and/or an acoustic matching layer).

However, unlike the ultrasound probe 12 described above with reference to FIGS. 1 and 2, the ultrasound probe 112 may be configured to be coupled to a separate auscultation device 114 including one or more acoustic receiver(s) 115 (e.g., a unidirectional acoustic receiver, such as a microphone) for capturing or detecting the auscultatory sounds generated by the body part(s) being imaged using the probe 112. As shown in FIG. 5, the separate auscultation device 114 may generally extend lengthwise between a sensing end 160 and an opposite, non-sensing end 162, with the acoustic receiver(s) 115 being positioned at or adjacent to the sensing end 160. In such an embodiment, the auscultation device 114 may be configured to be coupled to the ultrasound probe 112 such that the sensing end 160 of the auscultation device 114 is disposed at and/or adjacent to the detection end 118 of the probe housing 116. For example, in a particular embodiment, the sensing end 160 of the auscultation device 114 may define a contact surface 164 configured to be aligned with the corresponding contact surface 122 of the probe housing 116 when the auscultation device 114 is coupled to the ultrasound probe 112. As such, the aligned contact surfaces 122, 164 may, for example, be placed directly adjacent to the patient's skin during use of the enhanced ultrasound device 110.

Similar to the embodiment described above, the ultrasound probe 112 and the acoustic receiver(s) 115 of the auscultation device 114 may be configured to be communicatively coupled to a suitable computing device (e.g., computing device 28 of FIG. 2) such that the ultrasound image signals generated by the ultrasound probe 112 and the auscultation signals generated by the acoustic receiver(s) 115 may be transmitted to the computing device 28 and subsequently combined to produce a synchronized auscultatory ultrasound image. For example, as shown in FIG. 4, the ultrasound probe 112 and the acoustic receiver(s) 115 are coupled to the computing device 28 via a wired connection, such as by using suitable communicative cables 38. However, in alternative embodiments, the acoustic receiver(s) 115 and/or the ultrasound probe 112 may be coupled to the computing device 28 via a wireless connection. For instance, as will be described below, the auscultation device 114 may, in one embodiment, include a wireless transmitter configured to transmit the auscultation signals generated by the acoustic receiver(s) 115 to the computing device 28 for subsequent processing.

It should be appreciated that, by configuring the enhanced ultrasound device 110 to include an auscultation device 114 that is separately coupled to an ultrasound probe, the device 110 may be constructed by simply retrofitting an existing ultrasound probe with the disclosed auscultation device 114, thereby allowing a physician to conduct auscultatory ultrasounds without necessitating the purchase of a brand new ultrasound probe. In addition, since the auscultation device 114 may be detachably coupled to the ultrasound probe 112, the auscultation device 114 may also be configured to serve as a standalone device for conducting purely auscultatory examinations. For instance, as will be described below with reference to FIG. 5, the auscultation device 114 may include various components in addition to the acoustic receiver(s) 15, such as a speaker, a wireless transmitter, a power source and/or control features.

It should also be appreciated that the auscultation device 114 may be configured to be coupled to the ultrasound probe 112 using any suitable attachment or coupling means known in the art. For instance, as shown in the illustrated embodiment, one or more fastening clips 166 may be coupled to or formed integrally with the ultrasound probe 112. In such an embodiment, the auscultation device 114 may be easily coupled to and detached from the ultrasound probe 111 by simply inserting the device 114 within and removing the device 114 from the fastening clip(s) 116, respectively. Alternatively, the auscultation device 114 may be coupled to the ultrasound probe 112 using any other suitable means, such as mechanical fasteners (e.g., bolts, screws and the like), retaining brackets, hook-and-loop fasteners (e.g., Velcro), tape, glue and/or any other suitable attachment or coupling means.

Referring now to FIG. 5, a top view of one embodiment of a suitable auscultation device 114 that may be utilized as part of the enhanced ultrasound device 110 shown in FIG. 4 is illustrated in accordance with aspects of the present subject matter. As indicated above, the auscultation device 114 may include one or more acoustic receivers 115 for capturing auscultatory sounds. In addition, the auscultation device 114 may, optionally, include various other components that may, for example, allow for the device 114 to also serve as a stand-alone device for monitoring auscultatory sounds.

For example, as shown in FIG. 5, the auscultation device 114 may include a body or housing 170 configured to extend lengthwise between a sensing end 160 and an opposite, non-sensing end 162. As indicated above, the acoustic receiver(s) 115 may be configured to be positioned at or adjacent to the sensing end 160 of the device 114, such as by positioning the acoustic receiver(s) 115 within the housing 170 at or adjacent to a contact surface 164 defined at the sensing end 160.

It should be appreciated that the housing 170 may generally be configured to define any suitable shape. For instance, as shown in the illustrated embodiment, the housing 170 has a generally rectangular shape. However, in other embodiments, the housing 170 may have any other suitable shape, such as by configuring the housing 170 to define any suitable ergonomic shape that allows for the auscultation device 114 to be comfortably grasped by a user with one hand. In addition, the housing 170 may generally to define any suitable dimensions. However, in several embodiments, the housing 170 may be configured to be similar in size to a writing pen. For instance, in a particular embodiment, the housing 170 may define a length (measured horizontally relative to view shown in FIG. 5) ranging from about 5 centimeters (cm) to about 20 cm, such as from about 10 cm to about 15 cm and any other subranges therebetween. In such an embodiment, the housing may also define a width (measured vertically relative to the view shown in FIG. 5) and a height (measured into the page relative to the view shown in FIG. 5) ranging from about 1 cm to about 3 cm, such as from about 1.5 cm to about 2.5 cm and any other subranges therebetween.

In addition, the auscultation device 114 may, optionally, include a built-in speaker 172 coupled to the acoustic receiver(s) 115 to allow auscultation sounds detected by the receiver(s) 115 to be broadcast to the user. In such an embodiment, the speaker 172 may generally be configured to be positioned within the housing 170 at any suitable location that permits the sounds emitted from speaker 172 to be broadcast to persons positioned proximal to the device 114. For instance, as shown in FIG. 5, the speaker 172 may be positioned within the housing 170 adjacent to its non-sensing end 162. Additionally, as shown in FIG. 5, one or more sound channels 174 may be defined in the housing 170 adjacent to the speaker's location such that the sounds emitted from the speaker 172 may be broadcast outwardly from the housing 170.

Moreover, in embodiments in which the auscultation device 114 is not configured to communicate with a suitable computing device (e.g., computing device 28 of FIGS. 2 and 4) via a wired connection or as an alternative to using the wired connection, the device 114 may include a wireless transmitter 176 communicatively coupled to the acoustic receiver(s) 115 for transmitting the auscultation signals generated by the receiver(s) 115 to the computing device 28 via any suitable wireless communications protocol, such as the BLUETOOTH, WI-FI (802.11 b/g) and/or ZIGBEE wireless communication protocols. Such a wireless connection may be particularly advantageous when the auscultation device 114 is configured to be retrofit onto an existing ultrasound probe 112 to allow for an ultrasound and auscultatory examination to be performed simultaneously. Specifically, the wireless connection may allow for the auscultation device 114 to communicate with the computing device 28 coupled to the ultrasound probe 112 without requiring additional cables to be installed between the devices 28, 114.

In addition, the auscultation device 114 may also include a power source 178 configured to provide power to the various other components of the device 114, such as the receiver(s) 115, speaker 172 and the wireless transmitter 176. For instance, in one embodiment, the power source 178 may correspond to a rechargeable battery capable of meeting the power requirements of the various components of the auscultation device 114. In such an embodiment, the device 114 may be configured to be received within a corresponding docking station or mechanism (not shown) to allow the battery to be recharged or a suitable power cord may be connected to device 114 to recharge the battery. Alternatively, the power source 178 may correspond to any other suitable power source, such as a disposable battery.

Further, the auscultation device 114 may also include a suitable control mechanism 180 (e.g., a circuit board) for controlling one or more of the components of the device 114. In such an embodiment, as shown in FIG. 5, one or more control buttons or switches 182 may be associated with the control mechanism 180 to allow for the user to manually control the operation of the device 114, such as by allowing the user to turn on/off the acoustic receiver(s) 115 and/or to select whether the auscultation signals generated by the receiver(s) 115 will be transmitted wirelessly via the transmitter 176 to a separate computing device 28 and/or will be transmitted to the speaker 172 for immediately broadcasting the auscultatory sounds.

It should be appreciated that the auscultation device 114 shown in FIG. 5 is simply illustrated to provide one example of a separate device that may be utilized in combination with an ultrasound probe in order to provide a means for conducting simultaneous ultrasound and auscultatory examinations. In other embodiments, the auscultation device 114 may have any other suitable configuration and/or may include any other suitable combination of components.

As indicated above, the present subject matter is also directed to a method for conducting auscultatory examinations. For example, FIG. 6 illustrates a flow diagram of one embodiment of a suitable method 200 for conducting auscultatory examinations. As shown in FIG. 6, at (202), the method 200 includes receiving ultrasound image signals generated by an ultrasound probe. For instance, as indicated above, a suitable computing device may be coupled to the ultrasound probe for receiving the ultrasound image signals associated with the specific body part(s) being imaged.

In addition, at (204), the method 200 includes receiving auscultation signals generated by an acoustic receiver associated with the ultrasound probe. For instance, as indicated above, the acoustic receiver may, in one embodiment, be integrated into or otherwise incorporated within the ultrasound probe. Alternatively, the acoustic receiver may be included within a separate auscultation device configured to be separately coupled to the ultrasound probe. Regardless, the auscultation signals generated by the acoustic receiver may generally be associated with the sounds produced by the body part(s) being imaged as such body part(s) is actually being imaged using the ultrasound probe.

Moreover, at (206), the method 200 includes combining the ultrasound image signals and the auscultation signals to produce an auscultatory ultrasound image. Specifically, the moving ultrasound image generated using the ultrasound image signals may be synchronized with the sounds reproduced using the auscultation signals to provide a time-synchronized accusatory ultrasound image that relates the movement of the body part(s) being imaged to the sounds produced by such body part(s).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A system for conducting auscultatory ultrasounds, the system comprising:

an ultrasound probe including a housing having a detection end defining a contact surface, the ultrasound probe further including at least one transducer element and a backing disposed within the housing, the backing being configured to reduce back reflections associated with the ultrasound probe and being positioned within the housing such that the at least one transducer element is disposed between the backing and the contact surface, the at least one transducer element being configured to transmit transducer-generated ultrasound waves towards an object being imaged and receive reflected ultrasound waves corresponding to the transducer-generated ultrasound waves as reflected off of the object being imaged, the ultrasound probe being configured to generate ultrasound image signals based on the reflected ultrasound waves received by the at least one transducer element;

an acoustic receiver positioned within the housing, the acoustic receiver including a sensing end configured to receive object-generated sound waves originating from the object being imaged, the acoustic receiver being positioned adjacent to the at least one transducer element within the housing such that the sensing end of the acoustic receiver is positioned at a location between the contact surface and the backing, the object-generated sound waves differing from the transducer-generated ultrasound waves and the reflected ultrasound waves, the object-generated sound waves being associated with sounds generated by the object as the object is being imaged using the at least one transducer element, the acoustic receiver being further configured to generate auscultation signals based on the received object-generated sound waves; and a computing device communicatively coupled to the ultrasound probe and the acoustic receiver, the computing device being configured to combine the ultrasound image signals and the auscultation signals to produce an auscultatory ultrasound image, wherein the auscultatory ultrasound image corresponds to a synchronization of the sounds generated by the object with a moving ultrasound image produced based on the ultrasound image signals.

2. The system of claim 1, wherein the acoustic receiver comprises a unidirectional microphone.

3. The system of claim 1, further comprising a display and a speaker communicatively coupled to the computing device, the computing device being configured to transmit signals associated with the auscultatory ultrasound image to the display and the speaker for broadcasting auscultatory ultrasound image.

4. The system of claim 1, wherein the object comprises an internal organ.

5. An enhanced ultrasound device, comprising:

an ultrasound probe including a housing having a detection end defining a contact surface, the ultrasound probe further including at least one transducer element and a backing disposed within the housing, the backing being configured to reduce back reflections associated with the ultrasound probe and being positioned within the housing such that the at least one transducer element is disposed between the backing and the contact surface, the at least one transducer element being configured to transmit transducer-generated ultrasound waves towards an object being imaged and receive reflected ultrasound waves corresponding to the transducer-generated ultrasound waves as reflected off of the object being imaged, the ultrasound probe being configured to generate ultrasound image signals based on the reflected ultrasound waves received by the at least one transducer element; and an acoustic receiver positioned within the housing, the acoustic receiver including a sensing end configured to receive object-generated sound waves originating from the object being imaged, the acoustic receiver being positioned adjacent to the at least one transducer element within the housing such that the sensing end of the acoustic receiver is positioned at a location between the contact surface and the backing, the object-generated sound waves differing from the transducer-generated ultrasound waves and the reflected ultrasound waves, the object-generated sound waves being associated with sounds generated by the object as the object is being imaged using the at least one transducer element, the acoustic receiver being further configured to generate auscultation signals based on the received object-generated sound waves.

6. The enhanced ultrasound device of claim 5, wherein the acoustic receiver comprises a unidirectional microphone.

7. The enhanced ultrasound device of claim 5, wherein the ultrasound probe and the unidirectional acoustic receiver are configured to be communicatively coupled to a computing device, the computing device being configured to combine the Ultrasound image signals and the auscultation signals to produce an auscultatory ultrasound image.

8. The enhanced ultrasound device of claim 7, wherein the auscultatory ultrasound image comprises a synchronization of the sounds generated by the object with a moving ultrasound image produced based on the ultrasound image signals.

9. The enhanced ultrasound device of claim 7, wherein the object comprises an internal organ.

10. A method for conducting auscultatory ultrasounds, the method comprising:

receiving, with a computing device, ultrasound image signals generated by an ultrasound probe including a housing having a detection end defining a contact surface, the ultrasound probe further including at least one transducer element and a backing disposed within the housing, the backing being configured to reduce back reflections associated with the ultrasound probe and being positioned within the housing such that the at least one transducer element is disposed between the backing and the contact surface, the at least one transducer element being configured to transmit transducer-generated ultrasound waves towards an object being imaged and to receive reflected ultrasound waves corresponding to the transducer-generated ultrasound waves as reflected off of the object being imaged, the ultrasound probe being configured to generate the ultrasound image signals based on the reflected ultrasound waves received by the at least one transducer element;

receiving, with the computing device, auscultation signals generated by an acoustic receiver positioned within the housing, the acoustic receiver including a sensing end configured to receive object-generated sound waves originating from the object being imaged, the acoustic receiver being positioned adjacent to the at least one transducer element within the housing such that the sensing end of the acoustic receiver is positioned at a location between the contact surface and the backing, the object-generated sound waves differing from the transducer-generated ultrasound waves and the reflected ultrasound waves, the object-generated sound waves being associated with sounds generated by the object as the object is being imaged using the at least one transducer element, the acoustic receiver being further configured to generate the auscultation signals based on the received object-generated sound waves; and combining, with the computing device, the ultrasound image signals and the auscultation signals to produce an auscultatory ultrasound image, wherein the auscultatory ultrasound image corresponds to a synchronization of the sounds generated by the object with a moving ultrasound image produced based on the ultrasound image signals.

11. The method of claim 10, further comprising transmitting signals associated with the auscultatory ultrasound image to a display and a speaker for broadcasting the auscultatory ultrasound image.

12. The system of claim 1, wherein the acoustic receiver corresponds to a separate receiver than a receiver of the at least one transducer element.

13. The enhanced ultrasound device of claim 5, wherein the acoustic receiver corresponds to a separate receiver than a receiver of the at least one transducer element.

14. The method of claim 10, wherein the acoustic receiver corresponds to a separate receiver than a receiver of the at least one transducer element.

* * * * *